United States Patent
Sauli

[11] 4,062,951
[45] Dec. 13, 1977

[54] ORGANOPHOSPHORUS COMPOUNDS, COMPOSITIONS CONTAINING THEM AND THEIR METHOD OF USE

[75] Inventor: Michel Sauli, Lyon, France
[73] Assignee: Philagro S.A., Lyon, France
[21] Appl. No.: 665,871
[22] Filed: Mar. 11, 1976
[30] Foreign Application Priority Data
  Mar. 11, 1975  France .................. 75.07556
[51] Int. Cl.$^2$ .................. A01N 9/12; A01N 9/22; C07D 263/56; C07D 277/64
[52] U.S. Cl. .................. 424/200; 260/302 E; 260/307 D
[58] Field of Search .................. 260/307 D; 424/200
[56] References Cited
U.S. PATENT DOCUMENTS
2,877,155  3/1959  Metivier .................. 260/307 D
3,580,922  5/1971  Price, et al. .................. 260/307 D
3,674,803  7/1972  Scherer, et al. .................. 260/307 D

*Primary Examiner*—Donald G. Daus
*Assistant Examiner*—J. H. Turnipseed
*Attorney, Agent, or Firm*—Browdy and Neimark

[57] ABSTRACT

Organophosphorus compounds of the formula

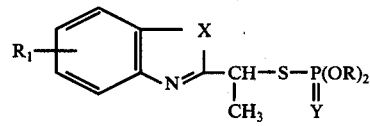

wherein R is alkyl of 1-4 carbons, $R_1$ is hydrogen, halogen, nitro, trifluoromethyl, or an alkyl, alkoxy or alkylthio radical of 1-4 carbons, and X and Y are sulfur or oxygen. The compounds are useful as insecticides and acaricides.

16 Claims, No Drawings

ORGANOPHOSPHORUS COMPOUNDS, COMPOSITIONS CONTAINING THEM AND THEIR METHOD OF USE

This invention relates to new organophosphorus compounds, to a process for their preparation and to compositions containing them.

The organophosphorus compounds of the present invention are those compounds of the general formula:

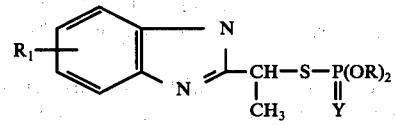
I wherein R represents an alkyl radical containing from 1 to 4 carbon atoms (preferably methyl or ethyl), $R_1$ represents a hydrogen or halogen (preferably chlorine) atom, or an alkyl, alkoxy or alkylthio radical, each such radical containing from 1 to 4 carbon atoms, or the nitro or trifluoromethyl radical, X represents a sulphur atom or preferably an oxygen atom, and Y represents an oxygen atom or preferably a sulphur atom.

According to a feature of the present invention, the organophosphorus compounds of general formula I are prepared by the process which comprises reacting a phosphorus compound of the general formula:

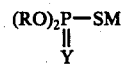
II (wherein M represents an alkali metal atom or an ammonium ion, and R and Y are as hereinbefore defined) with heterocyclic derivatives of the general formula:

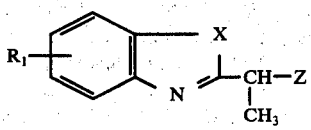
III wherein Z represents the acid residue of a reactive ester such as a halogen atom or a sulphonic or sulphuric acid residue, e.g. methylsulphonyloxy or methoxysulphonyloxy, and $R_1$ and X are as hereinbefore defined. The phosphorus compounds of formula II may optionally be prepared in situ.

The reaction is preferably carried out in an inert organic solvent and, more particularly, in an alcohol (e.g. methanol or ethanol), a ketone (e.g. acetone of methyl ethyl ketone), an ester (e.g. ethyl acetate), a nitrile (e.g. acetonitrile) or an aromatic hydrocarbon (e.g. benzene or toluene), at a temperature between 20° C. and the boiling point of the reaction mixture.

The hetrocyclic derivatives of general formula III may be obtained by the esterification of an alcohol of the general formula:

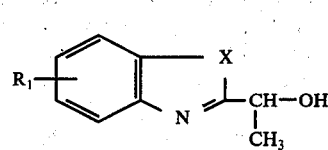
IV (wherein $R_1$ and X are as hereinbefore defined) by methods known per se for the preparation of reactive esters from alcohols. By the term "methods known per se" as used in this specification is meant methods heretobefore used or described in the literature.

The alcohols of general formula IV can be obtained by the action of lactic acid on an aniline derivative of the general formula:

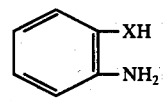
V wherein $R_1$ and X are as hereinbefore defined. Generally the reaction is effected in an organic solvent such as dichlorobenzene at the reflux temperature of the reaction mixture.

The organophosphorus derivatives of general formula I obtained by the afore-described process may optionally be purified by physico-chemical methods such as distillation, crystallisation or chromatography.

The organophosphorus compounds of general formula I possess useful insecticidal and acaricidal properties. They are particularly active through contact and by direct ingestion, especially against diptera, coleoptera, lepidoptera, orthoptera and acarids and more particularly against caterpillars.

Preferred compounds of general formula I are those wherein R represents a methyl or ethyl radical, $R_1$ represents a hydrogen or halogen (preferably chlorine) atom, X represents an oxygen atom and Y represents a sulphur atom, for example 2-(1-O,O-diethyldithiophosphoryl-ethyl) benzoxazole, 2-(1-O,O-dimethyldithiophosphoryl-ethyl)-benzoxazole and 5-chloro-2-(1-O,O-diethyldithiophosphoryl-ethyl) benzoxazole.

According to a further feature of the present invention, there are provided insecticidal and acaricidal compositions containing, as the active ingredient, at least one organophosphorus compound of formula I in association with one or more diluents or adjuvants compatible with the organophosphorus compound(s) and suitable for use in agricultural insecticidal and acaricidal compositions. Preferably the compositions contain between 0.005% and 95% by weight of organophosphorus compound.

The compositions may be solid if there is employed a powdered solid compatible diluent such as talc, calcined magnesia, kieselguhr, tricalcium phosphate, powdered cork, adsorbent charcoal, or a clay such as kaolin or bentonite. These solid compositions are preferably prepared by grinding the organophosphorus compound with the solid diluent, or by impregnating the solid diluent with a solution of the organophosphorus compound in a volatile solvent, evaporating the solvent, and if necessary grinding the product so as to obtain a powder.

Instead of a solid diluent, there may be used a liquid in which the organophosphorus compound is dissolved or dispersed. The compositions may thus take the form of suspensions, emulsions or solutions in organic or aqueousorganic media, for example acetophenone, aromatic hydrocarbons such as toluene or xylene or mineral, animal or vegetable oils, or mixtures of these diluents. The compositions in the form of suspensions, emulsions or solutions may contain wetting, dispersing or emulsifying agents of the ionic or non-ionic type, for example sulphoricinoleates, quaternary ammonium derivatives or products based on condensates of ethylene oxide, such as the condensates of ethylene oxide with octylphenol, or fatty acid esters of anhydrosorbitols which have been rendered soluble by etherification of the free hydroxyl groups by condensation with ethylene oxide. It is preferable to use agents of the non-ionic type because they are not sensitive to electrolytes. When emulsions are required, the organophosphorus compounds may be used in the form of self-emulsifying concentrates containing the active substance dissolved in the emulsifying agent or in a solvent containing an emulsifying agent compatible with the organophosphorus compound and solvent, a simple addition of water to such concentrates producing compositions ready for use.

The organophosphorus compounds of general formula I are preferably employed in a quantity of 40 to 60g. per hectoliter of water when they are used for spraying at a rate of between 300g. and 1 kg. per hectare.

The following Examples illustrate the preparation of organophosphorus compounds of general formula I.

EXAMPLE 1

A solution of ammonium O,O-diethyldithiophosphate (5.6 g.) in acetone (15 cc.) is added to a solution of 2-(1-methylsulphonyloxy-ethyl)benzoxazole (6 g.) in acetone (45 cc.). The reaction mixture is stirred for 24 hours at a temperature of about 20° C. After seperation of the precipitate formed and concentration of the filtrate under reduced pressure, the oily residue obtained (15 g.) is taken up in methylene chloride (70 cc.). The resulting organic solution is washed successively with distilled water (100 cc.), a 0.1N aqueous solution of sodium hydroxide (100 cc.) and distilled water (2 × 100 cc.). After drying over anhydrous sodium sulphate, discolouration with animal charcoal, filtration and concentration under reduced pressure, 2-(1-O,O-diethyldithiophosphoryl-ethyl)benzoxazole (7 g.) is obtained in the form of an oil ($n_D^{20} = 1.5718$).

2-(1-Methylsulphonyloxy-ethyl)benzoxazole (in the form of an oil) used as a starting material can be obtained by the action of methanesulphonyl chloride in solution in pyridine on 2-(1-hydroxyethyl)benzoxazole (b.p 104–107° C./0.3 mm,Hg), itself prepared by heating lactic acid with o-aminophenol in dichlorobenzene at the reflux temperature.

EXAMPLE 2

Following the procedure described in Example 1 but using ammonium O,O-dimethyldithiophosphate as starting material instead of ammonium O,O-diethyldithiophosphate, 2-(1-O,O-dimethyldithiophosphoryl-ethyl)benzoxazole is obtained in the form of an oil ($n_D^{20} = 1.5782$).

EXAMPLE 3

Following the procedure described in Example 1 but using 5-chloro-2-(1-methylsulphonyloxy-ethyl)-benzoxazole as starting material instead of 2-(1-methyl-sulphonyloxy-ethyl)benzoxazole, 5-chloro-2-(1-O,O-diethyldithiophosphoryl-ethyl)benzoxazole is obtained in the form of an oil ($n_D^{20} = 1.5772$).

The following Example illustrates compositions according to the present invention.

EXAMPLE 4

A condensation product of octylphenol and ethylene oxide containing 10 moles of ethylene oxide per mole of octylphenol (10 parts by weight) is added to a solution of 2-(1-O,O-diethyldithiophosphoryl-ethyl)-benzoxazole (25 parts by weight) in a mixture of equal parts (by volume) of toluene and acetophenone (65 parts by volume). The solution obtained is used, after dilution with water in the ratio of 200 cc. of this solution per 100 liters of water, to destroy greenfly, red spiders and caterpillars.

The insecticidal and acaricidal activities of the organophosphorus compounds of the present invention are demonstrated by the results obtained in the following tests:

a. Insecticidal activity through contact (fly, tribolium)

An acetone solution (1 cc.) of the product to be studied, at a given concentration, is sprayed into a 120 cc. glass pot. When the solvent has evaporated, the insects (5 flies or 10 triboliums) are placed in the pots, which are covered with a metal gauze. The number of dead insects after 24 hours' contact, in the case of the flies, and after 3 days' contact, in the case of the triboliums, is counted. The concentration which causes the death of 90% ($LC_{90}$) of the insects is determined.

| Product of | $LC_{90}$ | |
| --- | --- | --- |
| Example | Fly | Tribolium |
| 1 | $10^{-6}$ | $10^{-6}$ |
| 2 | $10^{-6}$ | $5 \times 10^{-7}$ |
| 3 | $3 \times 10^{-6}$ | $5 \times 10^{-6}$ | b. Insecticidal activity through contact [topical treatment of insects (fly, cricket)]

A known quantity of an aqueous acetone solution of the product to be studied is deposited with a micrometer syringe of the "Alga" type or of the "Hamilton" type on the prothorax of each insect, the amount being 0.001 cc. per fly or 0.003 cc. per cricket. The insects are anaesthetised with carbon dioxide. Various concentrations are used. The mortality is evaluated 24 hours after the treatment in the case of the flies and three days after the treatment in the case of the crickets. The concentration which causes 50% mortality ($LD_{50}$ in γ/insect) is determined.

| | $LD_{50}$ | |
| --- | --- | --- |
| Product of Example | Fly | Cricket |
| 1 | 0.2 | greater than or equal to 10 |
| 2 | 0.2 | 3 |
| 3 | 0.6 | greater than 10 | c. Insecticidal activity through contact-ingestion (foliage treated by dipping; caterpillars of *Plutella maculipennis* and caterpillars of *Pieris brassicae*)

Young cabbage leaves are dipped for 10 seconds in the solutions to be studied. When they are dried, they are infested with caterpillars (3rd stage) of *Plutella maculipennis* or *Pieris brassicae*. The mortality is determined 3 days after the treatment. The concentration which results in the 90% mortality (LC$_{90}$) of the caterpillars is determined.

| | LC$_{90}$ | |
|---|---|---|
| Product of Example | Plutella maculipennis | Pieris brassicae |
| 1 | $10^{-5}$ | $5 \times 10^{-6}$ |
| 2 | $3 \times 10^{-5}$ | $2 \times 10^{-5}$ |
| 3 | $10^{-5}$ | $10^{-5}$ | d. Acaricidal activity by contact-ingestion (foliage treated by dipping; *Tetracnychus telarius*, parthenogenetic females)

Leaves of bean plants at the cotyledon leaf stage are dipped for 10 seconds in the solution of the product to be studied. After drying, they are infested from leaves of heavily contaminated bean plants. The contaminated bean plants are kept alive by immersing the roots and the base of the stem in distilled water. The mortality is determined 2 to 4 days after contamination. The concentration which results in 90% mortality of the acarids (LC$_{90}$) is determined.

| | LC$_{90}$ |
|---|---|
| Product of Example | Tetranychus telarius |
| 1 | $3 \times 10^{-5}$ |
| 2 | $10^{-4}$ |
| 3 | $10^{-4}$ | e. Acaricidal-ovicidal activity through contact 10 mm. diameter discs are taken from bean leaves infested with *Tetranychus telarius*. The discs carrying 30 to 100 parthenogenetic eggs are immersed for 10 seconds in the solution of the product to be studied and are then fixed to a glass plate. Each disc is surrounded by a 3 to 5 mm. wide vaseline ring at a distance of about 5 mm. from the plurality of the disc. The number N of intact eggs is counted under a magnifying glass. The plates are kept at 25° C., for 7 days. The hexapod larvae immobilised in the ring of vaseline (n) are counted. The concentration of the product (LC$_{90}$) resulting in 90% mortality of the eggs (% of eggs killed = (N−n)/(N) × 100) is determined.

| | LC$_{90}$ |
|---|---|
| Product of Example | Tetranychus telarius |
| 1 | $10^{-3}$ |
| 2 | $2 \times 10^{-3}$ |
| 3 | $3 \times 10^{-4}$ |

What we claim is:
1. An organophosphorus compound of the formula:

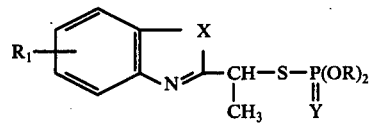

wherein R represents alkyl of from 1 to 4 carbon atoms, R$_1$ represents hydrogen or halogen, or alkyl, alkoxy or alkylthio, each such radical having from 1 to 4 carbon atoms, or nitro or trifluoromethyl, X is oxygen, and Y is oxygen or sulphur.

2. An organophosphorus compound according to claim 1 wherein R is methyl or ethyl.

3. An organophosphorus compound according to claim 1, wherein Y is sulphur.

4. An organophosphorus compound according to claim 3, wherein R is methyl or ethyl.

5. An organophosphorus compound according to claim 1, wherein R is methyl or ethyl, R$_1$ is hydrogen or halogen and Y is sulphur.

6. An organophosphorus compound according to claim 3 wherein R$_1$ is chlorine.

7. 2-(1-O,O-Diethyldithiophosphoryl-ethyl)benzoxazole.

8. 2-(1-O,O-Dimethyldithiophosphoryl-ethyl)benzoxazole.

9. 5-Chloro-2-(1-O,O-diethyldithiophosphoryl-ethyl)benzoxazole.

10. An insecticidal or acaricidal composition comprising, as active ingredient, an insecticidal- or acaricidal-effective amount of at least one organophosphorus compound as claimed in claim 5 in association with one or more diluents or adjuvents compatible with the organophosphorus compound(s) and suitable for use in agricultural insecticidal or acaricidal compositions.

11. Insecticidal or acaricidal composition according to claim 10 in which the quantity of organophorus compound is between 0.005% and 95% by weight of the composition.

12. Insecticidal or acaricidal composition according to claim 10 which contain a wetting, dispersing or emulsifying agent.

13. Insecticidal or acaricidal composition according to claim 12 wherein the wetting, dispersing or emulsifying agent is a non-ionic compound.

14. Insecticidal or acaricidal composition according to claim 12 in which the diluent associated with the phosphorus compound is water.

15. A method for killing insects and acarids comprising applying to said insects or acarids or to a locus expected to be infected with said insects or acarids, an amount effective to kill said insects and acarids of the compound of claim 1.

16. A method according to claim 15, comprising applying said active compound in a water spray of 40 to 60 grams per hl of water at a rate of between 300 grams and 1 kg per hectare.

* * * * *